US005171260A

United States Patent [19]

McIlwain

[11] Patent Number: 5,171,260

[45] Date of Patent: Dec. 15, 1992

[54] PASSIVE BODY-MOTION GENERATING APPARATUS AND PROCEDURE

[76] Inventor: William A. McIlwain, 7 S. Briarcliff Rd., Bristol, Tenn. 37620

[21] Appl. No.: 738,690

[22] Filed: Jul. 31, 1991

[51] Int. Cl.[5] .................. A61F 5/00

[52] U.S. Cl. .................. 606/243; 128/25 R

[58] Field of Search .................. 128/25 R, 71, 72, 73, 128/74, 70; 269/322, 323, 324, 325; 606/242, 243, 244

[56] References Cited

U.S. PATENT DOCUMENTS

| | | | |
|---|---|---|---|
| 2,152,431 | 3/1939 | Jensen | 128/74 |
| 2,598,204 | 5/1952 | Allen | 128/74 |
| 4,144,880 | 3/1979 | Daniels | 128/71 |
| 4,723,537 | 2/1988 | Parker, Jr. | 128/25 R |
| 4,827,913 | 5/1989 | Parker | 128/25 R |

*Primary Examiner*—Richard J. Apley
*Assistant Examiner*—Lynne Reichard

[57] ABSTRACT

A passive body-motion generating apparatus having a base, a lower body support, an upper body support, the top of each said suport providing a body contact surface, said supports each having a pivot end portion lying substantially adjacent each other, cooperating pivot mechanisms on each of the pivot end portions and base for allowing rotative motion of each body support through an arc sector, the pivot axes of the pivot mechanisms being substantially parallel and in proximity to each other, and a power train mechanism on the base in operative association with both body supports for imparting simultaneous rotative force thereto.

17 Claims, 3 Drawing Sheets

PASSIVE BODY-MOTION GENERATING APPARATUS AND PROCEDURE

FIELD OF INVENTION

The present invention concerns therapeutic, passive body-motion generating devices and therapeutic motion procedure, particularly those devices and procedures which are used for body rehabilitation purposes and which require little or no physical effort of the patient for producing the motion.

Patients who have experienced impact, twist or other damage, or who have undergone serious surgery of the back, e.g., of the lumbar region, particularly of the spine, are typically required, or at least advised, to essentially immobilize the back by maintaining a prone position for extended periods of time. In many cases however it has been recognized that some, even though slight motion of the damaged and/or adjacent areas of the back during recovery or rehabilitation has beneficial effects, for example, in enhancing blood flow to the area, in helping to maintain muscle strength and tone, and in maintaining a general feeling of activity and well-being in the patient.

DISCUSSION OF THE PRIOR ART

Many devices and apparatus for imparting motion to various parts of the body have been devised and include those shown in U.S. Pat. Nos.: 4,723,537; 4,802,462; 4,827,913; 3,039,456; 4,716,889; 3,060,926; 3,370,584; 4,860,734; 4,795,150; 4,834,073; and 3,071,130, the general disclosures of utility and structure such as various alternative drive or power means, bases or supporting frames, mechanical linkages for the drive means, body support means, cushioned body support pads or platforms, electrical control systems, or the like contained therein being incorporated herein by reference.

These prior art devices are no doubt therapeutically effective for the specific situations for which are designed, however, none of them relate to the necessities of the present rehabilitative or treatment problem. For example, the passive motion chairs or tables of the above U.S. Pat. Nos.: 4,723,537; 4,802,462; and 4,827,913, which applicant believes to be the most relevant prior art, have a gravitational aspect to their function, which cannot be tolerated in the present situation. For example, where injury or surgery has occurred with respect to the lumbar or other regions of the spine near or proximate thereto, any position of the body other than essentially horizontal can place a gravitational burden on the spine and adjacent tissue tending to compact the same, likely with anti-therapeutic effect.

Objects, therefore, of the present invention are: to provide a passive body-motion device or apparatus which can lightly and controllably move or flex regions of the back immediately adjacent an impaired segment thereof, and also the segment itself if desired, without placing a gravitational or other force burden thereon, while maintaining the segment in a substantially passive condition, and while imparting the salutory effects of the motion to the impaired segment; to provide such apparatus with motion degree adjustability, patient accessibility to drive control mechanism and with enhanced safety features; to provide a passive body-motion procedure which maintains substantial passivity of a back region being rehabilitated while providing intracorporeal activity to said region through the passive motion of adjacent back regions; to provide such apparatus with structural compactness and storage or transportation fold-up features; and to maximize the simplicity of construction and operation of such apparatus.

BRIEF SUMMARY OF THE INVENTION

The above and other objects hereinafter becoming evident have been attained in accordance with the present invention which in its apparatus embodiment is defined in its broad sense as a passive body-motion generating apparatus comprising base means, lower body support means, upper body support means, the top of each said support means providing body contact surface means, said support means having pivot end portions lying substantially adjacent each other, pivot means cooperatively mounted on each said pivot end portion and said base means for allowing independent rotative motion of each said support means with respect to said base means through an arc, the pivot axes of said pivot means being substantially parallel to each other and in proximity to each other, and power train means on said base means in operative association with both said support means for imparting simultaneous rotative force thereto.

In certain preferred apparatus embodiments:

(a) said power train means comprises motor means and eccentric linkage means connected thereto and to both said support means;

(b) said linkage means is provided with separate components for each support means, each of said components being individually adjustable in length with respect to its associated pivot means to selectively control the pivot arc angle of its associated support means;

(c) a stationary support for a back segment is provided on said base means intermediate said pivot end portions;

(d) said power train means is dimensioned to pivot both said support means from a substantially common plane upwardly through an arc angle of up to about twenty degrees;

(e) said power train means is provided with an optional lost motion safety disconnect means; and (f) said power train means is adapted to rotate each said body support means in an independent manner with respect to each other through its complete upward and downward rotation, i.e., cycle, at a frequency of from about 4.0 to about 15.0 cycles per minute, through an arc angle of up to about 25 degrees on each side of its horizontal plane.

In preferred passive body-motion procedure embodiments:

(g) the procedure for imparting passive motion to a lumbar region segment of the back, comprises the steps of supporting said segment in a substantially immoble, substantially horizontal posture while supporting upper and lower portions of the body adjacent thereto also in a substantially horizontal posture, simultaneously cycling said body portions in a substantially vertical rotative direction between lower and upper positions, said cycling causing slight flexing of the spine and surrounding body portions adjacent to each axial end (with reference to the spine longitudinal axis) of said segment, and/or the segment itself, to enhance intracorporeal physiological activity within said segment while said segment remains in a substantially passive condition; and (h) the procedure as in (g) wherein said cycling is through an arc angle of up to about 20 degrees on each side of a horizontal plane of said body portions with a frequency of from about 4.0 to about 15.0 cycles per minute.

BRIEF DESCRIPTION OF THE DRAWINGS

The invention will be further understood from the following drawings and description thereof wherein.

DETAILED DESCRIPTION OF THE DRAWINGS

Figure 1:
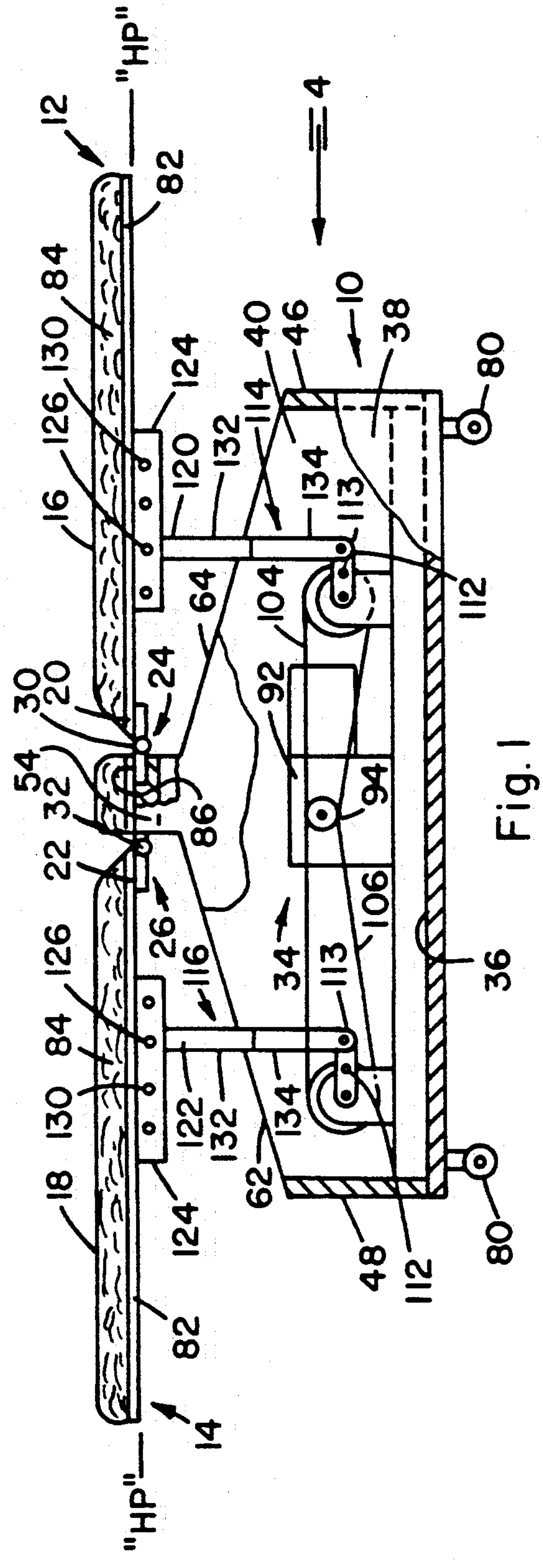
FIG. 1 is a side view of the apparatus with portions of the sidewall broken away to show details of the power train means.
Figure 2:
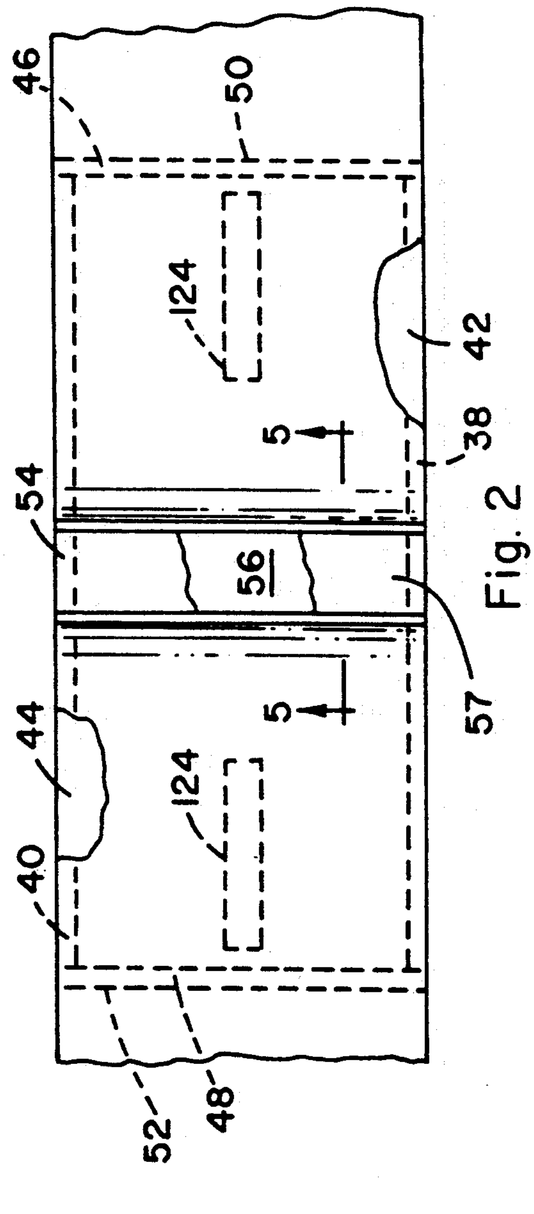
FIG. 2 is a top elevation of the apparatus of FIG. 1 in its folded down position.

Referring to the drawings and with reference to the claims hereof, the present invention is defined in its broad sense as a passive body motion generating apparatus comprising base means 10, lower body support means 12, upper body support means 14, the tops of said support means providing body contact surface means 16 and 18 respectively, said body support means having pivot end portions 20 and 22 lying substantially adjacent each other, cooperating pivot means 24 and 26 on said pivot end portions and said base means for allowing independent rotative motion of said support means through arc sector generally designated 27 and 28, the pivot axes 30 and 32 of said pivot means being substantially parallel and in proximity to each other, and power train means 34 on said base means in operative association with both said support means for imparting simultaneous rotative force thereto.

Figures 3, 4, 5, 6:
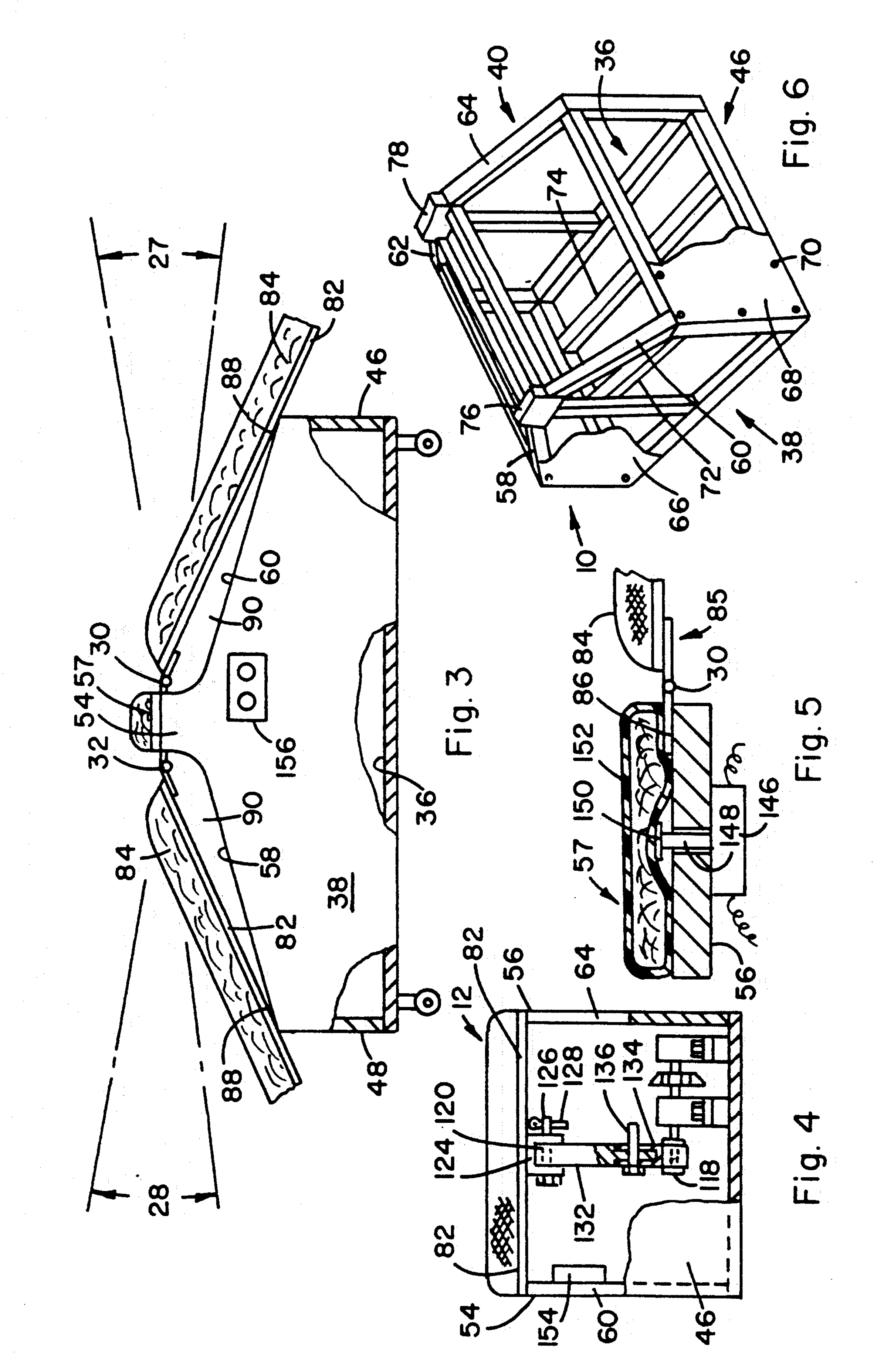
FIG. 3 is a side elevation of the apparatus of FIG. 1 in its folded down position.
FIG. 4 is an end view, partly in cross-section, of the apparatus of FIG. 1 as viewed in the direction of arrow 4 therein.
FIG. 5 is a cross-sectional view of the substantially stationary lumbar region support taken along line 5—5 of FIG. 2 in the direction of the arrows showing one embodiment of a cycle counter activating switch device.
FIG. 6 is an isometric view of a frame type base means for the present apparatus.

The base means 10 can be of any configuration and construction, however, the base as shown in the drawings has certain preferred features. As shown, the base comprises a floor 36 which may of solid material such as metal sheet, plywood, fiberboard, fiberglass sheet, or the like, or preferably, as shown in FIG. 6, constructed as a framework, e.g., from sections of square or rectangular metal tubing welded together in such array as to provide bolt receiving supports for mounting the pillow blocks and motor/gear reduction unit of the drive means in known manner. Sidewalls 38 and 40 are affixed to the base along the longitudinal edges 42, 44 respectively thereof, and endwalls 46 and 48 are affixed to the base along the lateral edges 50, 52 respectively thereof, by any suitable means such as screws, bolts, or other conventional fasteners.

Each sidewall of the base means is preferably configured and structured to provide substantially raised central portions generally indicated as 54 which are affixed to and bridged by lateral support means 56 which provides a base segment to which body supports 12 and 14 are affixed by means of the hinge or pivot means 24 and 26. The upper edge portions 58, 60 and 62, 64 respectively of sidewalls 38 and 40 preferably are sloped downwardly from portions 54 to allow a semi fold-up position of the body supports as described hereinafter in greater detail.

Shown in FIG. 6 is a preferred embodiment of the base means construction comprising welded together steel tubing sections to provide the sidewalls, endwalls and floor which are indicated generally by their respective characters. These metal sections are shown in exaggerated thicknesses for clarity, however, an adequate strength thereof must be provided to support the weight of very large persons. In this regard, additional diagonal bracing or the like connecting these sections may be provided as necessary. Portions of the sidewall and endwall facades 66 and 68 are shown in FIG. 6 and preferably comprise a cushioned, vinyl covered, highly attractive upholstery covering of about $\frac{1}{4}$ to $\frac{3}{8}$ in. thickness mounted on a fiberboard or the like backing of about $\frac{1}{8}$ in. thickness. These facades are attached by any suitable means such as metal clips or screws 70 to the metal tubing sections. The tubing sections 72 and 74 spanning the floor provide the necessary rigid supporting structure for mounting the drive train means as hereinafter described. The lateral support means 56 is not shown in FIG. 6 but may comprise a metal or wood plank or the like spanning and affixed to the tops 76, 78 of raised portions 54 by bolts or the like. The base is preferably provided with caster wheels 80 or the equivalent to allow easy movement and relocation of the apparatus.

Figure 9:
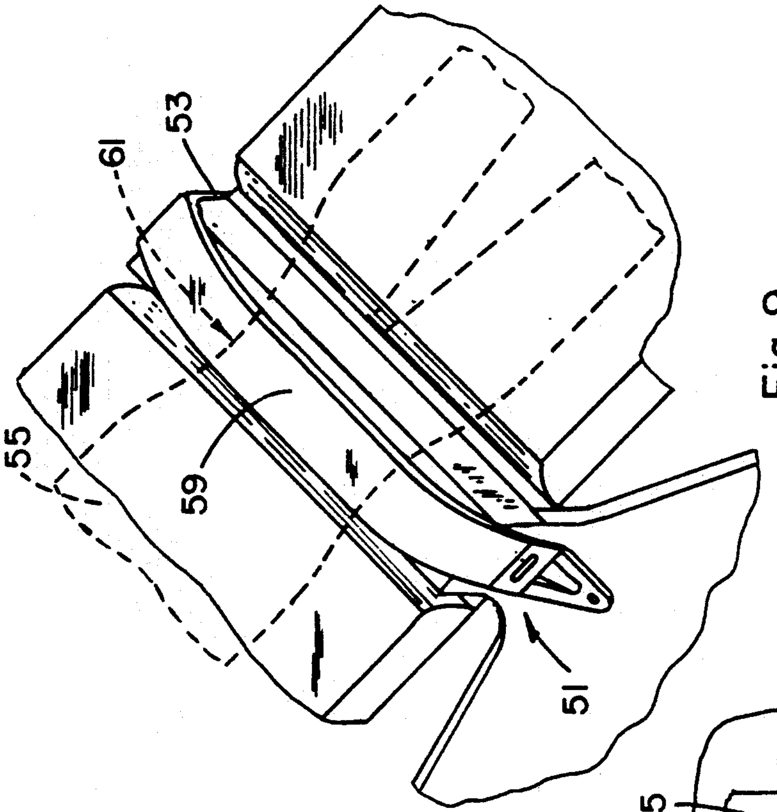
FIG. 9 is a perspective view of the safety or back segment passivity strap in use on a patient.

The lower and upper body support means 12 and 14 are essentially identical in construction and interchangeable with respect to the body portion, i.e., upper or lower, whichever each one supports. Each is comprised of a rigid, substantially flat bed member 82 and a cushion or pad 84, preferably having an attractive vinyl covering and affixed to the bed member in any conventional manner. Each bed member is affixed at its pivot end portion to one section of its pivot means 24 or 26, which e.g., can comprise a hinge such as 85 shown in FIG. 5, which extends substantially across the width of the pad, the other section of the pivot means being affixed to lateral support means 56 in any suitable manner such as by screws, bolts or the like, and preferably to the top 86 thereof, to allow the body support means to readily pivot and cycle through its aforesaid arc sector. The arc sector angle can be, e.g., 50 degrees on either side of the horizontal plane "HP", but is preferably up to about 25 degrees below and 45 degrees above said plane. These body supports are, of course, adequately dimensioned to accommodate large patients and typically are from 3–4 ft. in width and 3–5 ft. in length. The lateral support means 56 and its cushion or pad 57 can be varied in width depending on the area of the back which is intended to remain substantially passive during the rotative cyclical motion of the lower and upper body supports. Typically the width of this support means is from about 3–7 inches. In a preferred embodiment of the invention, a safety hold-down or body segment stabilizing strap means 59 of suitable material, e.g., padded vinyl, such as shown in FIG. 9 is provided and may be permanently attached at one end 53 to one side of the base and attachable to the other side of the base by, e.g., adjustable auto safety belt buckle means 51. In use, the strap is tensioned fairly tightly accross the body 55 shown in dotted outline in the area of the lumbar region 61 and maintains, when desired, substantial inflexibility and immobilization of the back segment under treatment.

It is particularly noted that the outer extremities 88 of upper edge portions 58, 60, 62 and 64 of the sidewalls provide a limiting stop means for downward rotation of the body supports such as occurs when the apparatus is placed in the aforesaid semifolded condition, but also in the event of failure or dislocation of the drive train linkage. In regard to the latter event, gaps 90 are provided between the upper edge portions of the sidewalls and the body supports to prevent damage to a patients hands or fingers which inadvertently may have been placed under the body support edges during the exercise procedure.

As seen more clearly from FIG. 1, the pivot end portions of the support pads 16 and 18 are preferably bevelled such that upward rotation of the support means will not be restricted, and also to provide a degree of isolation of the lateral support means from the main body support means to enhance the immobilization effect of the lateral or lumbar support.

Figure 7:
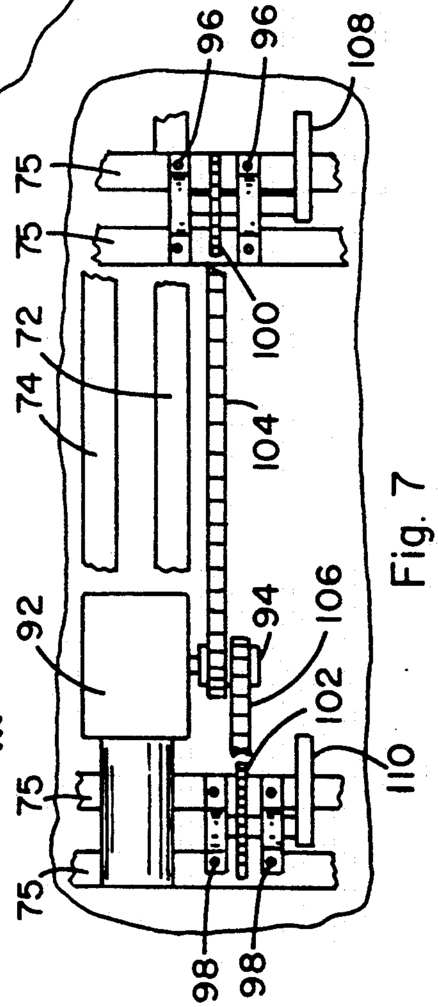
FIG. 7 is a top view schematic of the power train means.

The power train means may be of any type and construction which can impart upward, cyclical rotational force in a carefully regulated manner to the body support means 12 and 14. A useful and preferred type is shown in FIGS. 1 and 7 as comprising an electric motor/gear reduction unit generally designated 92 provided with a double chain sprocket 94 and bolted to floor 36 or to tubing sections 72, 74 in known manner. Also mounted to the floor or tubing sections such as the lateral tubing sections 75 are pillow block pairs 96 and 98 which support chain sprocket/shaft units 100 and 102 respectively. Chains 104 and 106 connect these sprocket/shaft units to the drive sprocket 94. Mounted on the sprocket shafts are eccentrics 108 and 110 which preferably are provided with a series of, e.g., four throw adjusting bearing apertures 112 to which the lower ends 113 of push rods 114 and 116 are each selectively, rotationally secured by shaft bolt means such as 118. The upper ends 120, 122 of these rods are rotationally secured to brackets such as 124 by shafts 126 which may be removably secured in placed by pins 128 (see FIG. 4) or the like slid through apertures in the shafts. The brackets are secured to the body supports by any suitable means such as screws, and are preferably provided with a series of rod mounting apertures 130 such that the angle at which the rods are affixed thereto can be adjusted to provide further adjustment of the arc angle through which each body support can be rotated.

Figure 8:
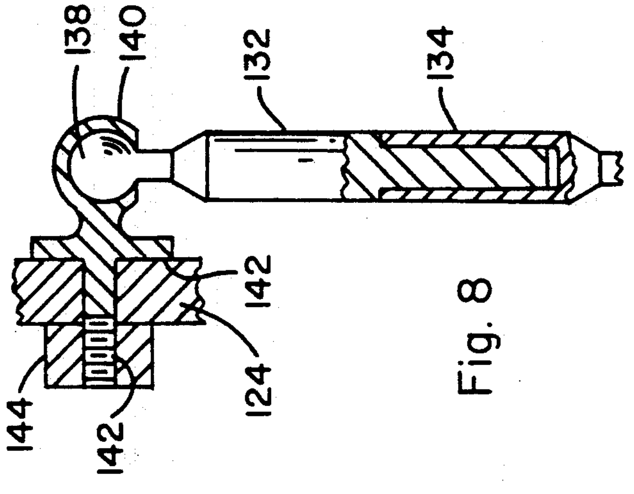
FIG. 8 is a partially sectioned view of a preferred structure for the push rods or struts and of their mounting elements.

In a preferred embodiment, each of the pushrods are provided in two telescoping sections 132 and 134 as shown in FIGS. 4 and 8. This construction allows separation of these sections should folding downwardly of the body supports be desired for transportation or the like. Also, when shaft 136 and a pin such as 128 are not employed to rigidly connect the rod sections together, a preferred safety feature is thus provided in that while the upward rotating force can be applied and maintained in a smooth manner to the body supports, the sections are readily separated on the down stroke of the rods should any portion of the body such as a hand, or any other obstruction find its way underneath the body supports. Through such separation of the rod sections, downward force generated by the drive means is immediately dislocated from the push rods and body supports.

Referring to FIG. 8, a preferred construction for the pushrod or strut end mountings is shown as comprising a ball 138 provided at each end of the strut and rotationally mounted within socket members 140 preferably integrally formed with a stop shoulder 142 and threaded shank segment 142 and adapted to be removably affixed to bracket 124 and eccentric 108 by nuts 144. Other types of known semi-universal motion mounting devices may also be employed.

Referring to FIG. 5, one or more electrical switching mechanisms such as 146 are mounted on lateral support member 56, preferably in at least one location where substantial body weight is certain to be applied during treatment. The actuating plunger 148 of the switch slidably extends through member 56 and is provided with a head 150 for contacting the underside of the covering 152 of pad 57 such that significant body weight will depress the plunger and activate an electrical circuit. This switching device is intended to actuate an electrically operated counter device only when a patient is actually on the body supports. The counter device is mounted, e.g., in a locked box 154 on the inside of the base sidewall, and accessible only to an attending physician, medical technician or the like for reading the number of rotative cycles of the body supports actually experienced by the patient. In a preferred embodiment, and elapsed time recorder is associated with the circuit to record the total elapsed time that the patient has been subjected to the passive motion. For example, a typical treatment period would be fifteen minutes at 4.0 cycles per minute, twice a day.

The drive means of the apparatus may be provided with a variable speed feature in known manner, and with a control mechanism including on-off switching, mounted, e.g., on the side of the apparatus on a control panel such as 156. Also, any remote or equivalent control system, such as a control cord and switch box may be employed, e.g., for patients who have great difficulty in moving and must have the control box in a readily accessible location, e.g., the immediate vicinity of their hand.

The invention has been described in detail with particular reference to preferred embodiments thereof, but it will be understood that variations and modifications will be effected within the spirit and scope of the invention.

We claim:

1. A passive body-motion generating apparatus for a lumbar region, back segment comprising base means, lower body support means, upper body support means, the top of each said support means providing body contact surface means, stationary, substantially flat lumbar region, back segment support means on said base means lying intermediate said pivot end portions, said back segment support means having a width of from about three to about seven inches, said body support means each having a pivot end portion lying substantially adjacent opposite sides of said back segment support means, pivot means cooperatively mounted on each said pivot end portion and said base means for allowing independent rotative motion of each said support means through an arc sector, the pivot axes of said pivot means being substantially parallel and in proximity to each other, and power train means on said base means in operative association with both said support means for imparting simultaneous rotative force thereto.

2. The apparatus of claim 1 wherein said power train means comprises motor means and eccentric linkage means connected thereto and to both said support means.

3. The apparatus of claim 2 wherein said linkage means is provided with separate components for each support means, each of said components being individually adjustable in length with respect to its associated pivot means to selectively control the pivot arc angle of its associated support means.

4. The apparatus of claim 2 wherein said power train means is dimensioned to pivot both said support means, independently, from a substantially horizontal plane upwardly through an arc angle of up to about 45 degrees, and downwardly through an arc angle of up to about 25 degrees.

5. The apparatus of claim 1 where said power train means is dimensioned to pivot both said support means, independently, from a substantially horizontal plane upwardly and downwardly through an arc sector of up to about twenty five degrees.

6. The apparatus of claim 2 wherein said base means is comprised of substantially rectangular floor means, and spaced sidewall means extending upwardly from opposite edges of said floor means, the upper edge portion of each said sidewall means being sloped from a portion thereof proximate said pivot end portions to provide a fold position support for each body support means, said linkage means being disconnectable from said body support means to allow the same to fold position downwardly and rest on said fold supports.

7. The apparatus of claim 6 wherein said body support means are substantially rectangular cushioned platforms.

8. The apparatus of claim 1 wherein said power train means is provided with lost motion safety means for disconnecting said body support means from said power train means upon the application of counter force to the downward motion of said body support under gravitational force.

9. The apparatus of claim 8 wherein said disconnect means comprises separate shoulder means within said power train means engageable with each other to transmit upward force to said body support means, but disengageable from each other upon cessation of said force.

10. The apparatus of claim 1 wherein said base means is provided with roller means for allowing easy movement of said apparatus.

11. The apparatus of claim 1 wherein a portion of said lumbar region support means is resiliently spring mounted on said base means for slight vertical motion under substantial body weight, pressure actuable electrical switch means mounted between said base means and said lumbar region support means, electrically operated counter means associated with one or more movable portions of said drive train means for recording the number of rotative cycles of said body support means, and electrical circuit means connecting said switch means to said counter means for placing said counter means in operation only when sufficient weight is applied to said lumbar region support means to force it into actuating engagement with said switch means.

12. A rehabilitation, passive body-motion generating procedure for a lumbar region segment of the back, comprising supporting said segment in a substantially immobile, substantially horizontal posture while supporting upper and lower portions of the body also in a substantially horizontal posture, simultaneously but independently cycling said body portions in a substantially vertical rotative direction between lower and upper positions, said cycling causing slight flexing of the spine and surrounding body portions immediately in the area of said segment or adjacent thereto to enhance intracorporeal physiological activity within said segment while said segment remains in a substantially passive condition.

13. The procedure of claim 12 wherein said cycling is through an arc angle on either side of a horizontal plane of up to about 25 degrees with a frequency of from about 4.0 to about 15.0 cycles per minute.

14. The procedure of claim 12 wherein said segment is held in a substantially immobile condition by strap means tensioned laterally accross the body in the area of said segment.

15. A passive body-motion generating apparatus for a lumbar region back segment comprising base means, lower body support means, upper body support means, the top of each said support means providing body contact surface means, each of said body support means having a pivot end portion lying substantially adjacent the other, pivot means cooperatively mounted on each said pivot end portion and said base means for allowing independent rotative motion of each said support means through an arc sector, the pivot axes of said pivot means being substantially parallel and in proximity to each other, and power train means on said base means in operative association with both said support means for imparting simultaneous rotative force thereto, said power train means being provided with lost motion safety means for disconnecting said body support means from said power train means upon the application of counter force to the downward motion of said body support under gravitational force.

16. The apparatus of claim 15 wherein said disconnect means comprises separate shoulder means within said power train means engageable with each other to transmit upward force to said body support means, but disengageable from each other upon cessation of said force.

17. A passive body-motion generating apparatus for a lumbar region back segment comprising base means, lower body support means, upper body support means, the top of each said support means providing body contact surface means, stationary, substantially flat lumbar region, back segment support means on said base means lying intermediate said pivot end portions, said body support means each having a pivot end portion lying substantially adjacent opposite sides of said back segment support means, pivot means cooperatively mounted on each said pivot end portion and said base means for allowing independent rotative motion of each said body support means through an arc sector, the pivot axes of said pivot means being substantially parallel and in proximity to each other, power train means on said base means in operative association with both said support means for imparting simultaneous rotative force thereto, and wherein a portion of said back segment support means is resiliently spring mounted on said base means for slight vertical motion under substantial body weight, pressure actuable electrical switch means is mounted between said base means and said back segment support means, electrically operated counter means is associated with one or more movable portions of said drive train means for recording the number of rotative cycles of said body support means, and electrical circuit means is provided connecting said switch means to said counter means for placing said counter means in operation only when sufficient weight is applied to said back segment support means to force it into actuating engagement with said switch means.

* * * * *